(12) United States Patent
Takami

(10) Patent No.: US 6,315,716 B1
(45) Date of Patent: *Nov. 13, 2001

(54) ENDOSCOPE AIR SENDING DEVICE

(75) Inventor: Satoshi Takami, Saitama (JP)

(73) Assignee: Asahi Kogaku Kogyo Kabushiki Kaisha, Tokyo (JP)

(*) Notice: Subject to any disclaimer, the term of this patent is extended or adjusted under 35 U.S.C. 154(b) by 0 days.

This patent is subject to a terminal disclaimer.

(21) Appl. No.: 09/391,349

(22) Filed: Sep. 8, 1999

(30) Foreign Application Priority Data

Sep. 9, 1998 (JP) .................................. 10-255107

(51) Int. Cl.$^7$ ...................................... A61B 1/12
(52) U.S. Cl. ..................... 600/158; 600/159; 600/560; 137/565.18; 417/44.2
(58) Field of Search .................... 600/156, 158, 600/159, 560; 604/23, 26; 137/565.18; 417/44.2

(56) References Cited

U.S. PATENT DOCUMENTS

| 4,863,355 | * | 9/1989 | Odagiri et al. ................. 417/12 |
|---|---|---|---|
| 4,969,801 | * | 11/1990 | Haseley et al. ................. 417/18 |
| 4,971,034 | | 11/1990 | Doi et al. . |
| 5,377,688 | | 1/1995 | Aviv et al. . |
| 5,515,860 | | 5/1996 | Aviv et al. . |
| 6,193,649 | * | 2/2001 | Takami et al. ................. 600/158 |

* cited by examiner

Primary Examiner—Linda C. M. Dvorak
Assistant Examiner—Jocelyn Ram
(74) Attorney, Agent, or Firm—Greenblum & Bernstein P.L.C.

(57) ABSTRACT

An endoscope air sending device (15) has a compressor (13), an air tank (34), an air filter (35), a pressure control valve (38), a pressure sensor (14), and a discharge valve (12) are provided. The compressor and the air tank are communicated with each other through an air tube (AT5), and the air tank and the air filter are communicated with each other through an air tube (AT4). The air filter and the discharge valve are communicated with each other through an air tube (AT3), and the pressure control valve, the air sensor and the discharge valve are also communicated with one another through the air tube (AT3). By communicating those components with one another in the above-described manner, a closed space is formed.

11 Claims, 6 Drawing Sheets

DUST
(MATERIAL ACCUMULATED INTERNALLY)

ENDOSCOPE AIR SENDING DEVICE

BACKGROUND OF THE INVENTION

This invention relates to an endoscope air sending device for sending air into a body cavity such as the stomach, and more particularly to the arrangement of components including valves and a compressor which are provided for sending air into the body cavity.

An endoscope air sending device is known in the art which is so designed that the air whose pressure is increased by an air compressor is discharged by controlling a valve, and the air thus discharged is sent into the body cavity through a tube. In the device, during discharging, the compressor is operated while a pressure control valve controls the pressure of the air to be discharged. The pressure control valve adjusts the sectional area of the air flowing path, to thereby control the pressure of the air.

The pressure control valve is only able to decrease the pressure of the air to be discharged. Therefore, it is necessary to provide a large compressor of high output type which can send a high pressure air. However, as the compressor is of the higher output type, it generates more noise. Hence, during the medical operation, the compressor operating at all times is noisy. Furthermore, because of the structure of the pressure control valve, the endoscope air sending device cannot discharge the air with fine pressure adjustment. The endoscope air sending device cannot accurately perform the air pressure control over a wide range of from low pressure to high pressure.

SUMMARY OF THE INVENTION

Accordingly, an object of the invention is to provide an endoscope air sending device in which a closed space is provided to make it possible to discharge a higher pressure air even if a low output type compressor (which outputs a low pressure air) is used, as well as to accurately perform pressure control. Another object of the present invention is to provide an endoscope air sending device in which elements forming the closed space are appropriately arranged, whereby the pressure control is achieved stably.

The foregoing object of the invention has been achieved by the provision of an endoscope air sending device, which comprises:

a compressor which compresses air and sends the air thus compressed into a closed space;

an air tank which is a part of the closed space;

an air filter adapted to remove dust from the closed space;

a pressure sensor adapted to measure a pressure of the closed space, a pressure control valve which, in order to adjust the pressure of the closed space according to the pressure of the closed space measured by the pressure sensor, discharges the air from the closed space; and a discharge valve for discharging the air from the closed space, and in which the compress or and the air tank are communicated with each other through a first air tube, the air tank and the air filter are communicated with each other through a second air tube, and the air filter, the pressure control valve, the pressure sensor and the discharge valve are communicated with one another through a third air tube, thereby forming the closed space.

In the endoscope air sending device, it is preferable that the air tank is cylindrical.

It is preferable that two connectors are provided on the air tank in order to communicate the air tank with the first and second air tubes, the connectors being L-shaped and mounted on both end surfaces of the air tank, respectively, in such a manner that the two connectors are confronted with each other.

It is preferable that the two connectors are located above the centers of the end surfaces of the air tank.

It is preferable that the first air tube is communicated with one of the two connectors, which is located farther from the compressor than the other.

It is preferable that the first and second air tubes are arranged along the air tank.

It is preferable that the third air tube is a tube for communicating the air filter and the discharge valve with each other, and the tube is branched, extending towards the pressure sensor and towards the pressure control valve.

It is preferable that the pressure control valve and the pressure sensor, being communicated with each other through the third air tube, are arranged near each other.

The present disclosure relates to the subject matter contained in Japanese patent application No. Hei. 10-255107 (filed on Sep. 9, 1998), which is expressly incorporated herein by reference in its entirety.

DESCRIPTION OF THE PREFERRED EMBODIMENT

Figure 1:
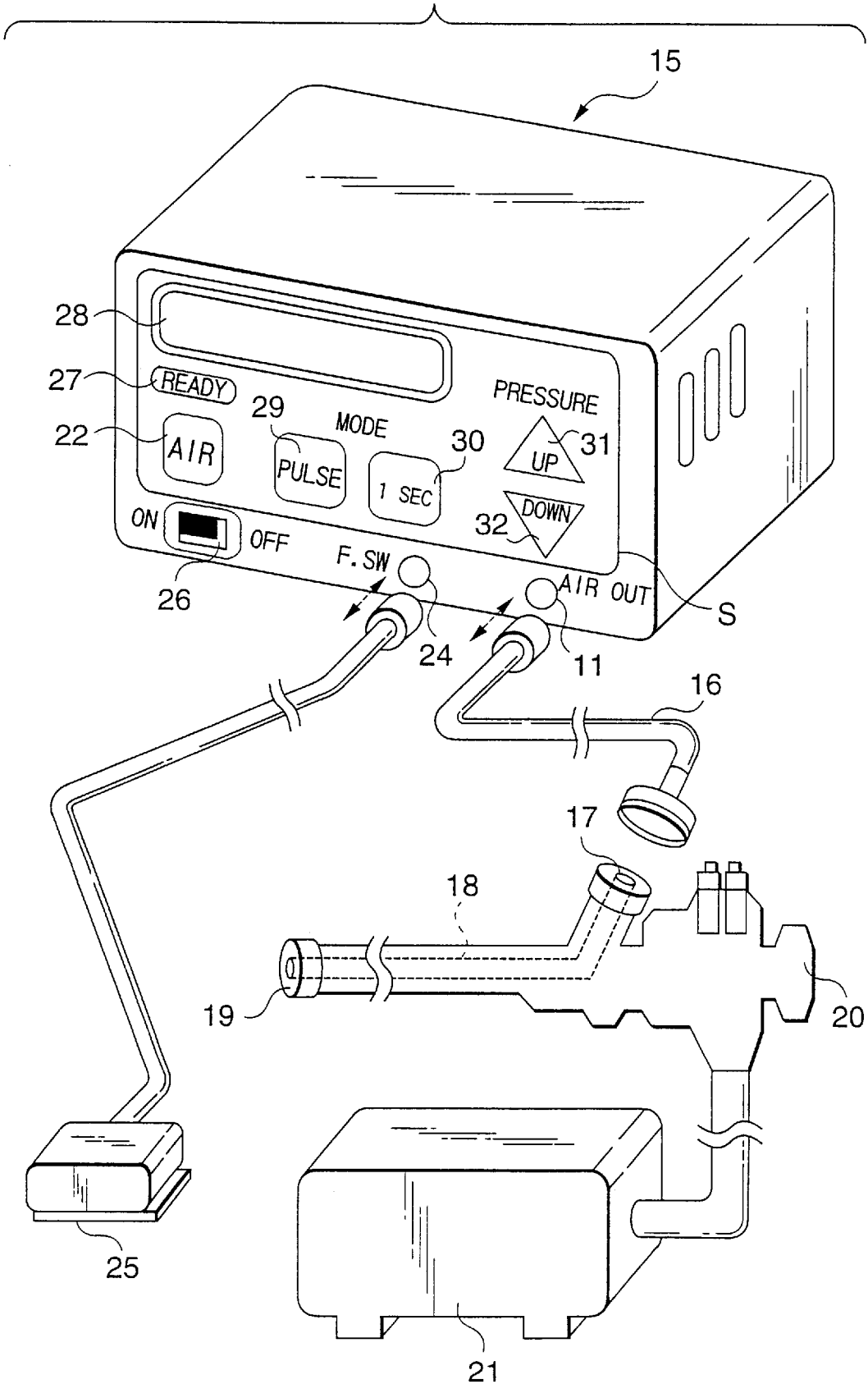
FIG. 1 is a perspective view showing an endoscope air sending device, which constitutes a preferred embodiment of the invention.

An embodiment of the invention will be described with reference to the accompanying drawings. FIG. 1 is a perspective view of an endoscope air sending device, which constitutes the embodiment of the invention. The endoscope air sending device is to send air into a body cavity such as the stomach for inspection of the affected part.

The endoscope air sending device 15 is provided at its front surface with an operating panel S, a main switch 26, and connectors 11 and 24. The operating panel S has pressure setting switches and other various switches.

The main switch 26 is to supply current to an electrical circuit in the device 15. A discharging switch 22 is to discharge air from a closed space formed in the device 15. More specifically, when the discharging switch 22 is turned on, the air is discharged through the connector 11. A lamp 27 is to display, when the pressure of the air in the closed spaced reaches a predetermined value, the fact that the air discharging operation has become ready. A display section 28 displays a value of an air pressure to be set.

A pulse switch 29 is to discharge the air in a pulse mode. A one-second switch 30 is to discharge the air for one second. An up switch 31 and a down switch 32 are to set the pressure of the closed spaced.

The connector 11 is connected to a connecting tube 16, so that, as the air is discharged, the air is sent into the body cavity through the connecting tube 16. The connector 24 is connected to the power supply cord of a foot switch 25 so that the remote control of the air discharging operation is enabled.

The other end of the connecting tube 16 (which is not connected to the connector 11) is connected to a forceps inlet 17 of an endoscope 20. The forceps inlet 17 is communicated through a forceps channel 18 to a forceps outlet 19. A path for allowing the air to flow is defined between the connector 11 and the forceps outlet 19, so that the air discharged from the connector 11 is sent through the forceps outlet 19 into the body cavity. The image of the body cavity is formed on an image pickup element (not shown) provided within an endoscope 20, and displayed on a monitor (not shown) in an animation mode with the aid of a processor 21.

Figure 2:
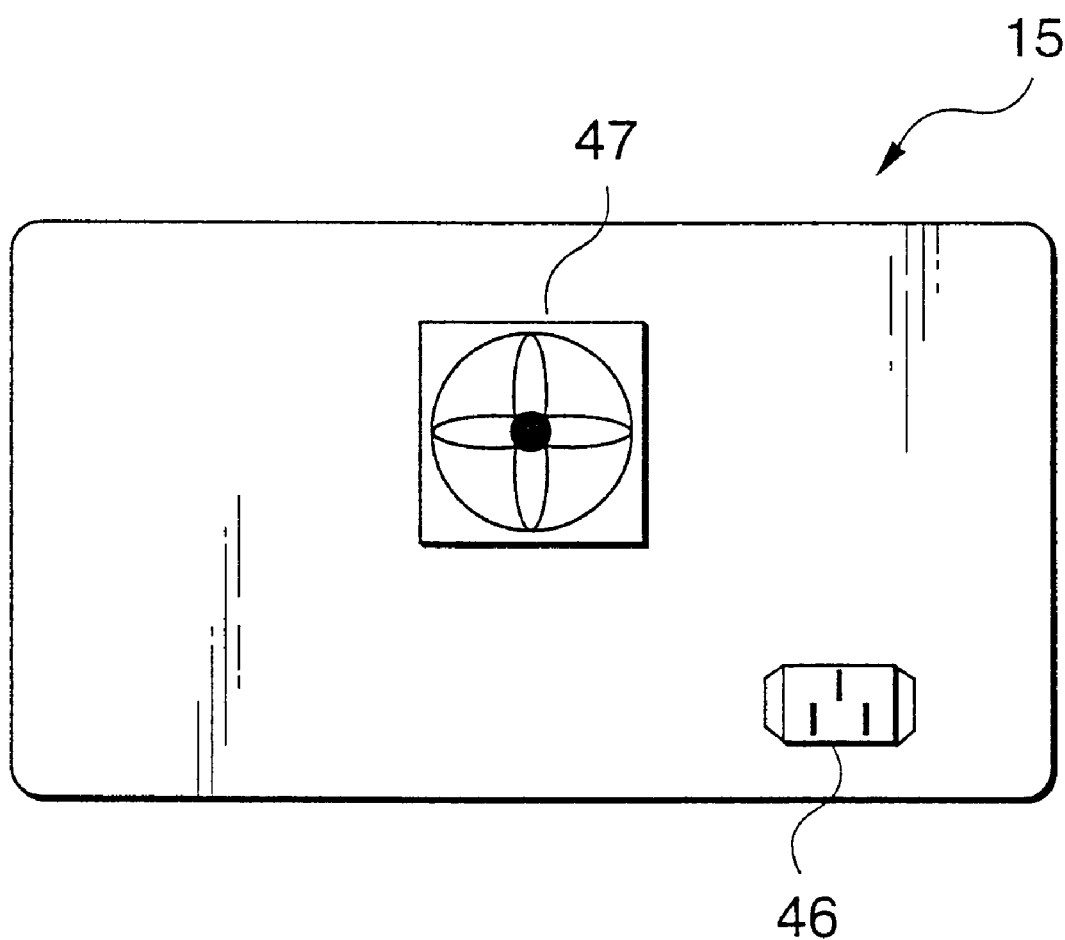
FIG. 2 is a rear view of the endoscope air sending device.

FIG. 2 is a rear view of the endoscope air sending device 15. A DC fan 47 for sending air to cool the inside of the endoscope air sending device 15, and an AC inlet 46 through which current is received from the commercial power source are provided as shown in FIG. 2.

Figure 3:
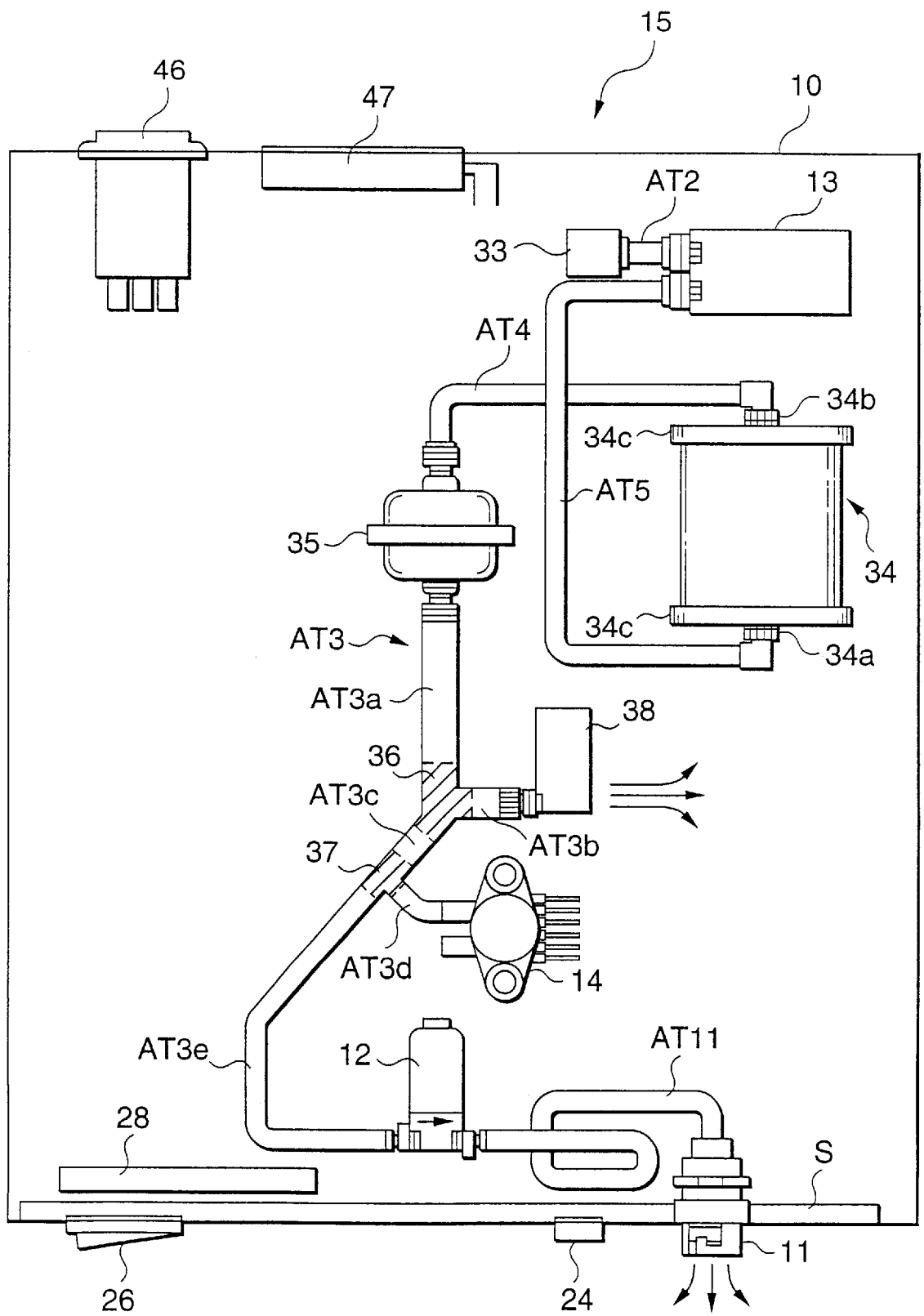
FIG. 3 is a plan view of the inside of the endoscope air sending device.

FIG. 3 is a top view showing the arrangement of essential components (except the electrical circuit and the wiring) inside the endoscope air sending device 15. The AC inlet 46, the DC fan 47, the main switch 26, the operating panel S including the display section 28, and the connector 24 are arranged on the walls of the housing 10.

The closed space for discharging air is formed inside the housing 10. This closed space is formed by the compressor 13, an air tube AT5 (a first air tube), an air tank 34, an air tube AT4 (a second air tube), an air filter 35, an air tube AT3 (a third air tube), and a discharge valve 12 which are communicated with one another in the stated order. The air in the closed space is discharged through an air tube AT11 from the connector 11.

The air tube AT3 is of branch type. That is, the closed space is branched towards the pressure control valve 38 by a bifurcated section 36 of the air tube AT3, and towards the pressure sensor 14 by a bifurcated section 37. In the embodiment, the air tube AT3 is made up of five parts, namely, tubes AT3$a$, AT3$b$, AT3$c$, AT3$d$ and AT3$e$. The air tubes are pipes through which air flows.

In the case where the pressure of the closed space is adjusted or the air in the closed space is discharged, the air in the closed space is sent outside thereof. The pressure control valve 38 is normally closed, but opened when the pressure of the air in the closed space is decreased. The discharge valve 12 is normally closed, but opened when the discharging switch 22 or the foot switch 25 is operated.

A silencer 33 for decreasing the volume of noise made when the compressor is in operation, is connected through the air tube AT2 to the air suction inlet (not shown) of the compressor 13. When the compressor 13 is operated, the air flowing in through the silencer 33 and the air tube AT2 is compressed, and sent into the closed space, whereby the pressure of the air in the closed space is increased.

The air tank 34 is cylindrical, and is provided for the purpose of increasing the volume of the closed space. The volume of the air tank 34 is much larger than the total volume of the air tubes AT3 through AT5. In the embodiment, in order to discharge air stably for one second, the air tank has a volume of one liter. On the end surfaces 34$c$ of the air tank 34, connectors 34$a$ and 34$b$ are provided to which the air tubes AT5 and AT4 are connected, respectively. The air tube AT5 is connected to the connector 34$a$ which is located farther from the air compressor 13 than the connector 34$b$.

The air filter 35 is provided to remove dust from the air in the closed space. The pressure of the air in the closed space is measured with the pressure sensor 14. of the air tube AT3, the tubes AT3$a$, AT3$b$ and AT3$c$ are larger in diameter (sectional area) than the tubes AT3$d$ and AT3$e$. Furthermore, of the air tube AT3, the tubes AT3$b$, AT3$c$ and AT3$d$ are short so that the pressure control valve 38 and the pressure sensor 14, being communicated with each other through the air tube AT3, are located close to each other.

The pressure control valve 38 is operated to set the pressure of the closed space as required, thereby adjusting the pressure of the closed space. When it is determined that the pressure of the closed space measured by the pressure sensor 14 is lower than the set value (pressure), the compressor 13 operates, and the pressure control valve 38 is closed. In this case, the pressure control valve 38 and the discharge valve 12 secure the sealed closed space, and thus no air leakage from the closed space occurs. Hence, the pressure within the closed space can quickly reach to the set value for the air pressure. Even with a low output type compressor, the pressure within the closed space can be made higher, because the low output type compressor can output more air into the closed space and compress the air therein. When it is determined that the pressure of the closed space is higher than the set value, the compressor 13 is stopped, and the pressure control valve 38 is opened. In the case where the pressure of the closed space is equal to the set value, the compressor 13 is not operated (stopped), and the pressure control valve 38 is closed. In this case, the pressure control valve 38 and the discharge valves 12 are both closed to secure the sealed closed space, to thereby maintain the air pressure within the closed space at the set value until the discharge valve 12 is opened.

When the discharging switch 22 or the foot switch 25 is operated, the discharge valve 12 is operated. When the discharge valve 12 is opened, the air is discharged through the air tube AT11 from the connector 11.

Figure 4:
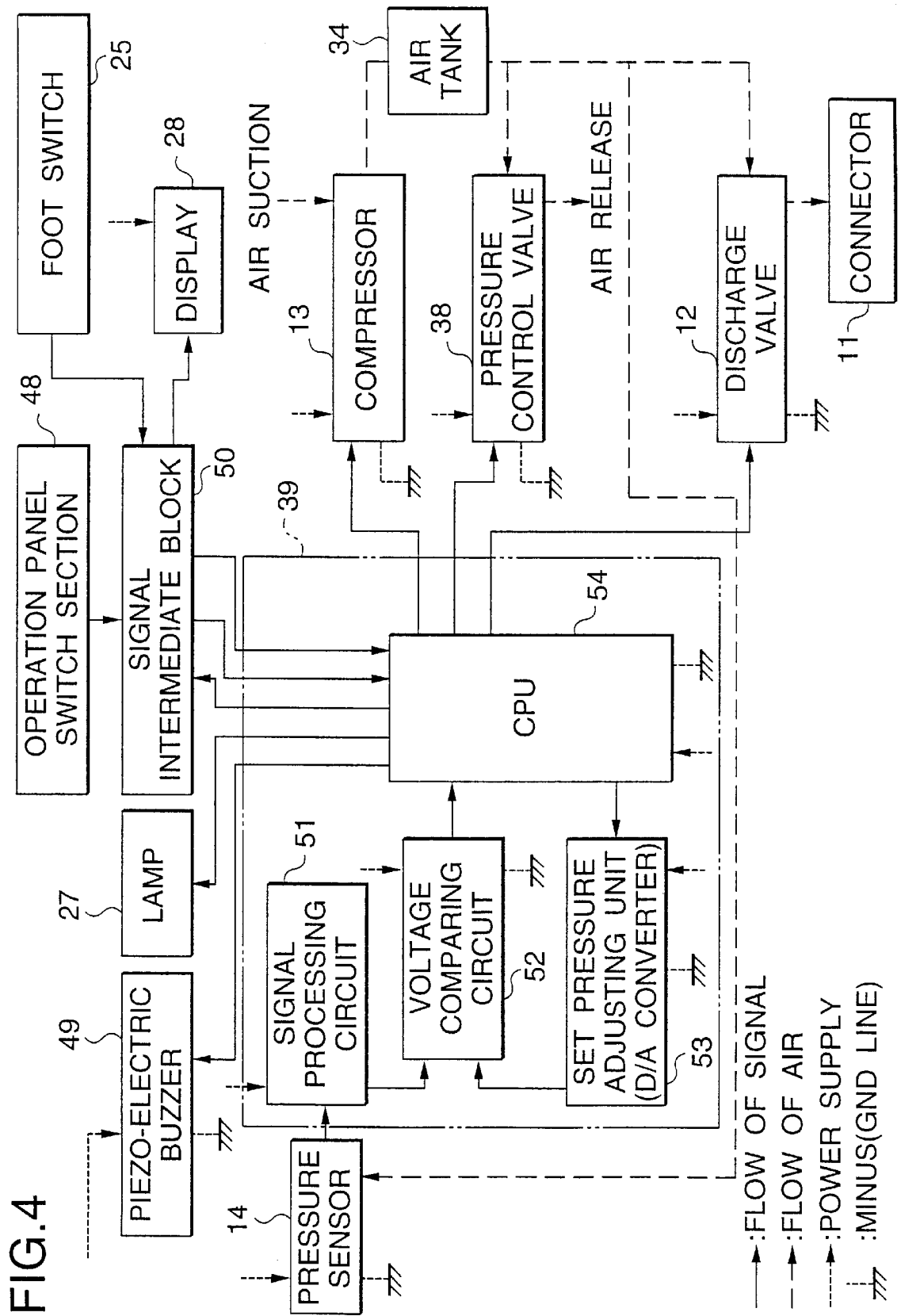
FIG. 4 is a block diagram showing an electrical circuit in the endoscope air sending device.

FIG. 4 is a block diagram showing the electrical circuit of the embodiment.

A control circuit 39 comprises a signal processing circuit 51, a voltage comparison circuit 52, a set pressure adjusting unit 53, and a CPU 54, and controls the whole operation of the endoscope air sending device 15. The CPU 54 outputs drive signals to a piezo-electric buzzer 49, the lamp 27, the compressor 13, the pressure control valve 38, and the discharge valve 12.

The operating panel switch section 48 generates signals upon the operation of the discharge switch 22, the pulse switch 29, the one-second switch 30, the up switch 31 and the down switch 32. The signals outputted by the operating panel switch section 48 and the foot switch 25 are transmitted through a signal intermediate block 50 to the CPU 54. In the signal intermediate block 50, the signals transmitted from the operating panel switch 48 are subjected to predetermined processes, or converted into signals which can be handled by the CPU 54. The signal concerning the pressure which has been set by the operations of the up switch 31 and the down switch 32 is applied through the signal intermediate block 50 to the display section 28.

The output signal of the pressure sensor 14 is inputted to the signal processing circuit 51, where it is processed for instance to remove noise therefrom. The signal thus processed is applied to the voltage comparison circuit 52. On the other hand, according to the signal concerning the set pressure which is inputted to the CPU by the operations of the up switch 31 and the down switch 32, a digital signal is applied to the set pressure adjusting unit 53 (a D/A converter). The digital signal is converted into an analog signal by the set pressure adjusting unit 53, which is then transmitted to the voltage comparison circuit 52.

The voltage comparison circuit 52 compares the signal from the signal processing circuit 51 with the signal (voltage signal) from the set voltage adjusting unit 53. A signal generated as a result of the comparison is converted into a signal of a certain voltage level, which can be handled by the CPU 54, and then transmitted to the CPU 54. The CPU 54 judges whether or not the pressure of the air in the closed space is equal to the set pressure based on the signal transmitted from the voltage comparison circuit 52.

In the case where the voltages compared with each other by the voltage comparison circuit 52 are substantially equal to each other, such a hunting operation may occur that the start and stop of the compressor 13 and the opening and closing of the pressure control valve 38 are repeated. In order to eliminate such hunting operation, a dead voltage zone or non-sensible voltage zone is preliminarily set for the comparison voltage range.

The piezo-electric buzzer 49 generates a buzzer sound in response to each switch operation. When the air discharging operation is ready, the lamp 27 is turned on.

Electric power is supplied to the power source circuit (not shown) through the AC inlet 46 and the main switch 26 so that respective predetermined voltages are applied to the display section 28, the pressure sensor 14, the CPU 54, the air compressor 13, the pressure control valve 38, and the discharge valve 12.

Figure 5:
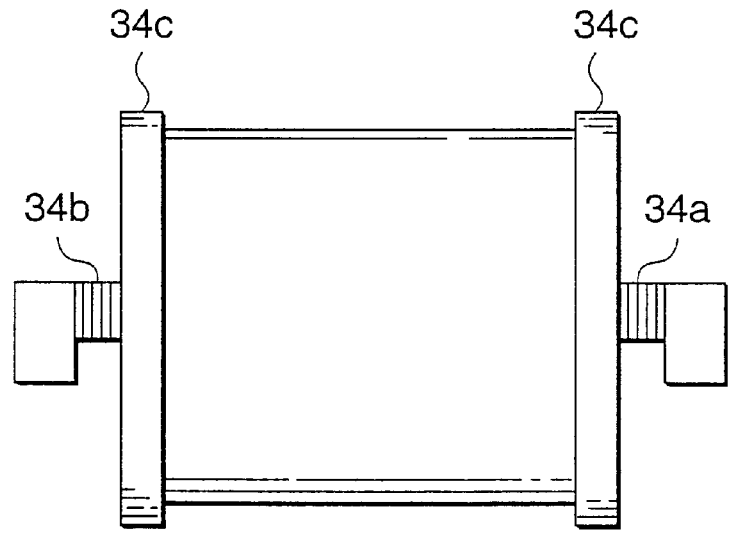
FIG. 5 is a plan view of an air tank in the endoscope air sending device.
Figure 6:
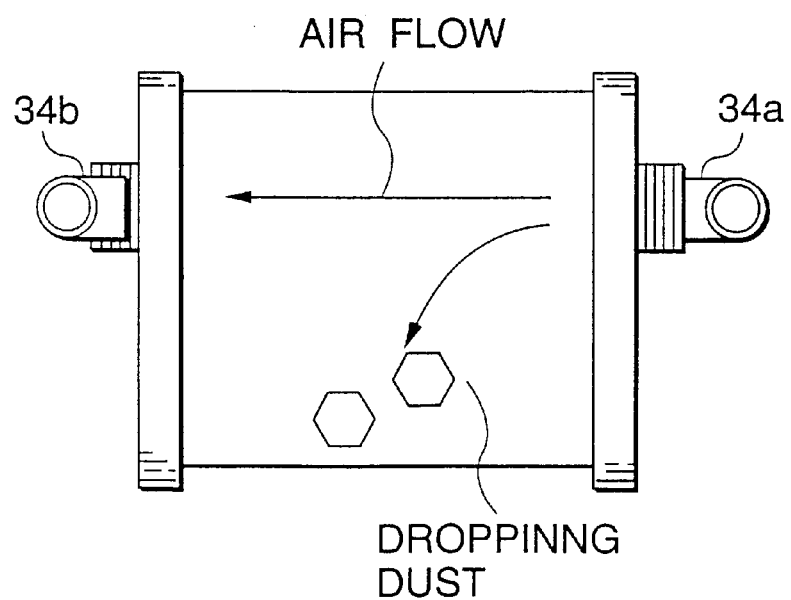
FIG. 6 is a front view of the air tank.
Figure 7:
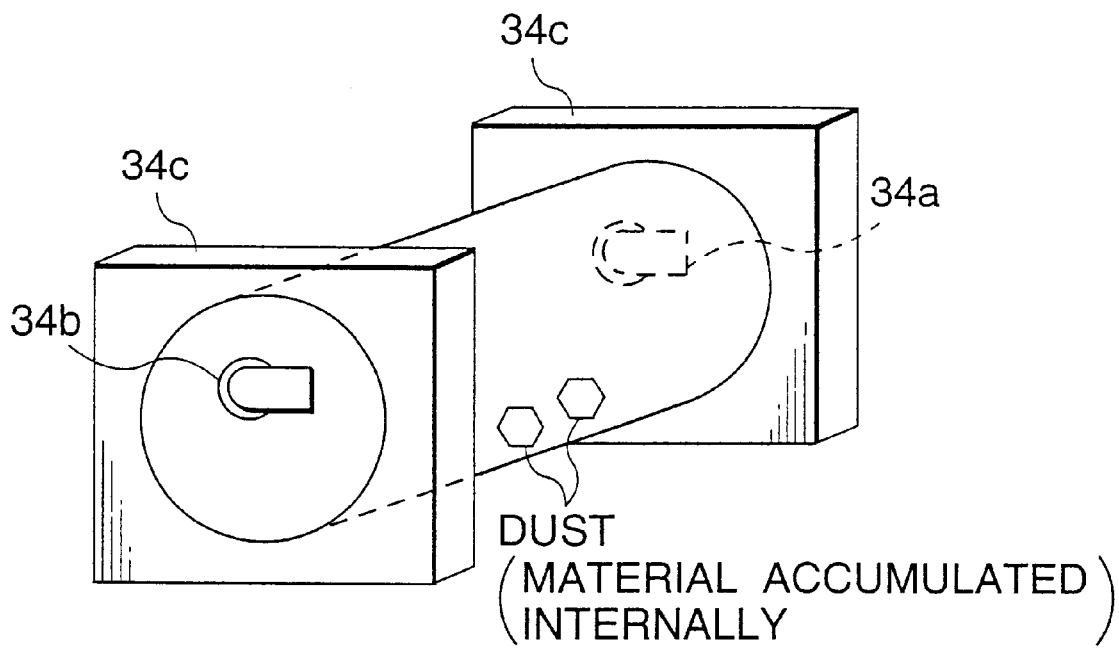
FIG. 7 is a perspective view of the air tank.
Figure 8:
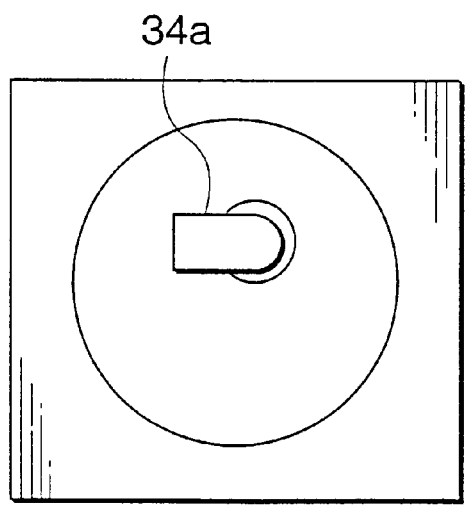
FIG. 8 is a side view of the air tank.

FIG. 5 is a plan view of the air tank 34, FIG. 6 is a front view of the air tank 34, FIG. 7 is a perspective view of the air tank 34, and FIG. 8 is a side view of the air tank 34. The air tank 34 adapted to remove dust from the air in the closed space will be described with reference to FIGS. 5 through 8.

As the inner surfaces of the compressor 13 rub against each other, dust is formed; or dust is mixed in the air which is sucked in through the compressor 13. Hence, dust is liable to be caught in the closed space.

As shown in FIG. 5, a plan view of the air tank 34, the air tank 34 is cylindrical, and has connectors 34a and 34b on respective end surfaces 34c for connection to the air tubes AT4 and AT5. The connectors 34a and 34b are L-shaped so as to avoid unnecessary bending of the air tubes AT4 and AT5. The connectors 34a and 34b are arranged so as to be confronted with each other. Hence, the air tubes AT4 and AT5 are arranged along the air tank 34. That is, the air tubes AT4 and AT5 can be arranged to extend in parallel to the end surfaces 34c of the air tank 34.

The front view of FIG. 6, and the perspective view of FIG. 7 show the inside of the air tank 34, in which dust in the closed space drops. Since the air tank 34 is large in volume, as air flows in the air tank 34, the heavy dust mixed in the air drops and is accumulated in the bottom of the air tank 34.

As can be seen from the front and side views, i.e. FIGS. 6 and 8, the connectors 34a and 34b are located above the centers of both end surfaces 34c of the air tank 34. Hence, the dust thus dropped scarcely flows into the air tubes AT4 and AT5 again.

The connectors 34a and 34b are mounted on the end surfaces 34c in such a manner as to be confronted with each other. Therefore, in the air tank 34, convection of the air will not unnecessarily occur; that is, the stream of air flowing in the air tank 34 is stable. Therefore, the dust caught in the air tank 34 scarcely moves up and down, and accordingly scarcely flows into the air tubes AT4 and AT5.

The air tank has the above-described structure, and therefore it serves as a filter for removing dust from the air.

As was described above, the start and stop of the compressor 13, and the opening and closing of the pressure control valve 38 are controlled according to the pressure of the closed space measured by the pressure sensor 14, so that the pressure of the closed space can be adjusted to the set pressure. The air thus pressure-controlled can be discharged into the body cavity as the discharge valve 12 is opened. In addition, in response to the change in the set pressure, the pressure of the closed space is adjusted and thus the air discharge pressure is adjusted. Since it suffices that the discharge valve 12 is controlled to simply provide either of a full open state or a full closed state without adjusting the sectional area of the air flowing path, the valve mechanism and its control mechanism can be made simple.

Since the air tank 34 serves as a filter, the air filter 35 is scarcely clogged up with dust; that is, the pressure control can be performed stably. Furthermore, since the air tube AT5 is connected to the connector 34a of the air tank 34 which is far from the compressor 13, the vibration of the compressor 13 is absorbed by the air tube AT5 and is scarcely transmitted directly to the air tank 34. Hence, all the components of the endoscope air sending device 15 are stable against the vibration; that is, the device is improved in reliability as much.

The pressure sensor 14 and the pressure control valve 38, which are connected through the air tube AT3, are arranged close to each other, so that the pressure variation which occurs when the pressure control valve 38 is opened is quickly transmitted to the pressure sensor 14. Furthermore, the pressure sensor 14 and the compressor 13 are located far from each other, and therefore the vibration of the compressor 13 is not transmitted to the pressure sensor 14. Hence, the pressure of the closed space can be detected in a real time mode, and the stable pressure control is achieved.

In the air tube AT3, the tubes AT3a, AT3b and AT3c are larger in diameter than the tubes At3d and AT3e. Therefore, even at the bifurcated sections 36 and 37 where the direction of flow of the air changes, great eddies are scarcely formed. Hence, when the set pressure is changed, the pressure of the closed space can be changed stably.

The air tube AT3 may be divided into plural sections, and the bifurcated sections 36 and 37 may be replaced with couplings to connect the divided sections of the air tube AT3.

As is apparent from the above description, according to the invention, the provision of the closed space in the air sending device makes it possible to perform the pressure control with accuracy, and the suitable arrangement of the components forming the closed space makes it possible to perform the pressure control with stability.

What is claimed is:

1. An endoscope air sending device, comprising:

a compressor which compresses air and sends the air thus compressed into a closed space;

an air tank which is a part of said closed space;

an air filter adapted to remove dust from said closed space;

a pressure sensor adapted to measure a pressure of said closed space;

a pressure control valve which, in order to adjust the pressure of said closed space according to the pressure of said closed space measured by said pressure sensor, discharges the air from said closed space; and a discharge valve which discharges the air from said closed space, and wherein said compressor and said air tank are communicated with each other through a first air tube, said air tank and said air filter are communicated with each other through a second air tube, and said air filter, said pressure control valve, said pressure sensor and said discharge valve are communicated with one another through a third air tube, thereby forming said closed space.

2. An endoscope air sending device as claimed in claim 1, wherein said air tank is cylindrical.

3. An endoscope air sending device as claimed in claim 1, wherein said air tank has two L-shaped connectors for communicating with said first and second air tube, and said two connectors are mounted on respective end surfaces of said air tank in such a manner that said two connectors are opposite each other.

4. An endoscope air sending device as claimed in claim 3, wherein said two connectors are located above centers of said end surfaces of said air tank.

5. An endoscope air sending device as claimed in claim 3, wherein said first air tube is communicated with one of said two connectors, which is located farther from said compressor than the other.

6. An endoscope air sending device as claimed in claim 1, wherein said first and second air tubes are arranged along said air tank.

7. An endoscope air sending device as claimed in claim 6, wherein said first and second air tubes are arranged in parallel to end surfaces of said air tank.

8. An endoscope air sending device as claimed in claim 1, wherein said third air tube is branched.

9. An endoscope air sending device as claimed in claim 8, wherein said third air tube has first and second bifurcated sections in a path between said air filter and said discharge valve, said first bifurcated section defines a branched path extending towards said pressure sensor, and said second bifurcated section defines a branched path extending towards said pressure control valve.

10. An endoscope air sending device as claimed in claim 9, wherein said first and second bifurcated sections are integrally formed in said third air tube.

11. An endoscope air sending device as claimed in claim 1, wherein said pressure control valve and said pressure sensor, being communicated with each other through said third air tube, are arranged close to each other.

* * * * *